US00PP26824P2

(12) United States Plant Patent
Irie

(10) Patent No.: US PP26,824 P2
(45) Date of Patent: Jun. 14, 2016

(54) ***HYDRANGEA* PLANT NAMED 'INSPIRE'**

(50) Latin Name: *Hydrangea macrophylla*
Varietal Denomination: Inspire

(71) Applicant: Ryoji Irie, Kyoto (JP)

(72) Inventor: Ryoji Irie, Kyoto (JP)

( * ) Notice: Subject to any disclaimer, the term of this patent is extended or adjusted under 35 U.S.C. 154(b) by 227 days.

(21) Appl. No.: 13/999,145

(22) Filed: Jan. 21, 2014

(51) Int. Cl.
*A01H 5/00* (2006.01)

(52) U.S. Cl.
USPC ..... Plt./250

(58) Field of Classification Search
USPC ..... Plt./226, 250
See application file for complete search history.

(56) References Cited

PUBLICATIONS

Concept Plants; *Hydrangea macrophylla* Inspire PPAF. 2014 www.conceptplants.com/plant/?p=hyminsp. Accessed Oct. 30, 2015.*
Concept Plants Breeders. 2014 www.conceptplants.com/breeders/. Accessed Oct. 30, 2015.*
FarWest Portland 2016. Inspire *Hydrangea*. www.farwestshow.com/nvs.shtml. Accessed Oct. 30, 2015.*
PLUTO: Plant Variety Database, Oct. 30, 2015, citation for 'H19-20'.*

* cited by examiner

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Hydrangea macrophylla* named 'Inspire' that is characterized by its free-flowering and re-blooming habit, and its large well-developed mop-head type inflorescences comprised of double sterile flowers that are clear light pink in color and mature in color to a blend of pale pink and light green, its long, strong stems and its fertile flowers that do not open.

2 Drawing Sheets

Genus/species: *Hydrangea macrophylla.*
Varietal denomination: 'Inspire'.

BACKGROUND OF THE INVENTION

The present invention relates to a new and distinct cultivar of *Hydrangea macrophylla* and will be referred to hereafter by its cultivar name, 'Inspire'. 'Inspire' represents a new bigleaf *hydrangea*, a perennial shrub grown for landscape use.

'Inspire' was derived from an ongoing controlled breeding program by the Inventor that focuses on developing new cultivars of bigleaf *hydrangeas* with unique flower colors and double flowers. 'Inspire' originated from a cross conducted in the Inventor's trial garden in June 1996 in Kyoto, Japan between an unnamed plant of *Hydrangea macrophylla* from the Inventor's breeding collection as the female parent and *Hydrangea macrophylla* 'Yamaajisai' (not patented) as the male parent. The new *Hydrangea* was selected as a unique single plant from the progeny of the cross in 2002.

Asexual reproduction of the new cultivar was first accomplished by by softwood stem cuttings in Kyoto, Japan in 2002 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Inspire' as a unique cultivar of *Hydrangea macrophylla.*

1. 'Inspire' exhibits double sterile flowers that are clear light pink in color and mature in color to a blend of pale pink and light green.
2. 'Inspire' exhibits a free flowering and repeating blooming habit; blooming from early May through early October in The Netherlands.
3. 'Inspire' exhibits large well-developed mop-head type inflorescences.
4. 'Inspire' exhibits long, strong stems.
5. 'Inspire' exhibits fertile flower buds that do not open.

'Inspire' can be compared to its male parent, 'Yamaajisai', which differs from 'Inspire' in having sterile flowers with sepals that are less clear pink, in having a smaller flatter formed inflorescence, and in having shorter and weaker stems. 'Inspire' can be compared to its female parent, which differs from 'Inspire' in having fertile flowers that open and in having smaller inflorescences. 'Inspire' can be most closely compared to the cultivars 'Youmenine' (U.S. Plant Pat. No. 16,613) and 'FREEDOM' (U.S. Plant Pat. No. 22,210). 'FREEDOM' differs from 'Inspire' in having whitish to light pink flowers. 'Youmenine' differs from 'Inspire' in having stems that are much shorter with shorter internode lengths, sterile flower buds that are obovate in shape rather than ovate, and sterile flower sepals that are darker pink in color with more acute apices than those of 'Inspire'.

BRIEF DESCRIPTION OF THE DRAWINGS

The photographs in the figures were taken of a five year-old plant of 'Inspire' as grown under unheated greenhouse conditions with ambient light in a 5-liter container in De Kwakel, The Netherlands.

The photograph in FIG. 1 illustrates a side view of 'Inspire' in bloom.

Figure 1:
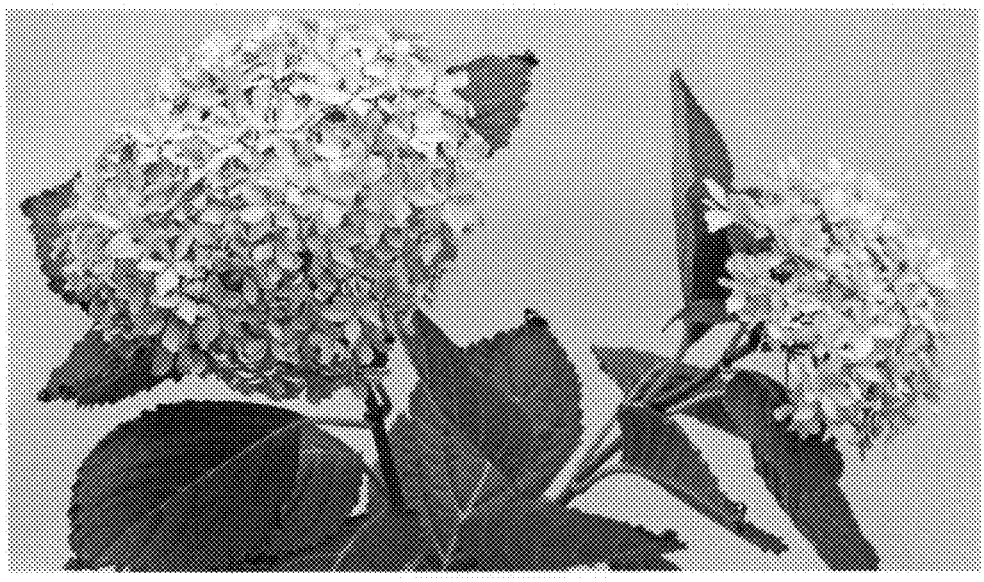
Figure 2:
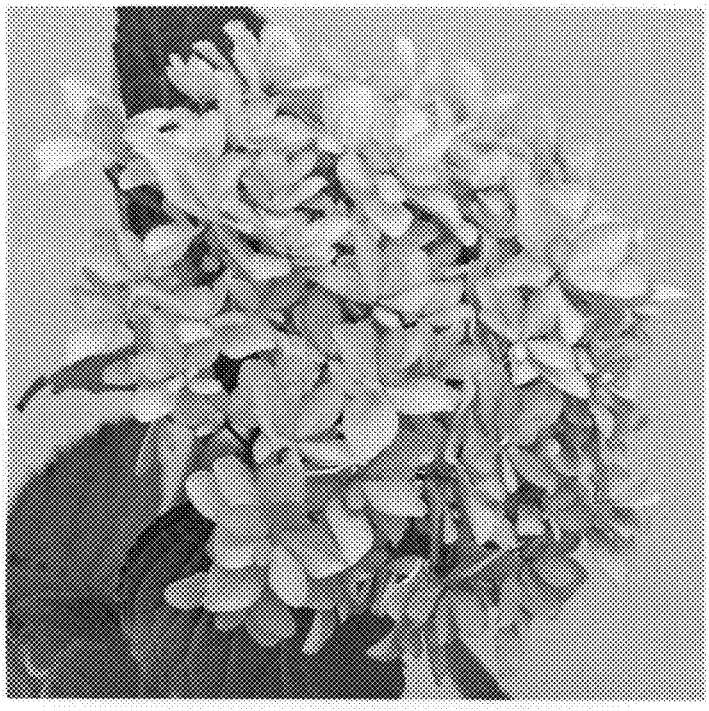

The photograph in FIG. 2 provides a close-up view of an inflorescence at peak color of 'Inspire'.

Figure 3:
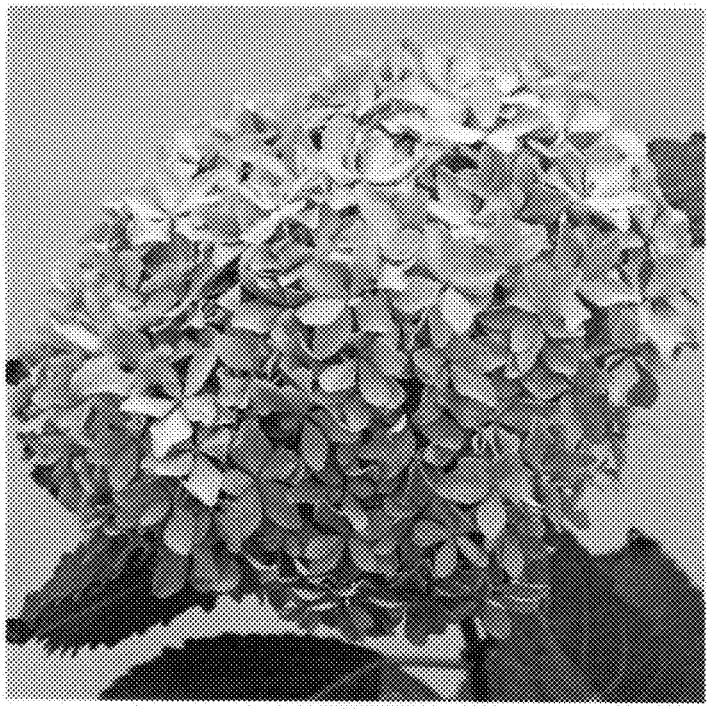

The photograph in FIG. 3 provides a close-up view of a maturing inflorescence of 'Inspire'.

The colors in the photographs are as close as possible with the digital photography and printing techniques utilized and the color codes in the detailed botanical description more accurately describe the new *Hydrangea.*

BOTANICAL DESCRIPTION OF THE PLANT

The following is a detailed description of two year-old plants as grown under greenhouse conditions in five-liter containers in an unheated greenhouse in De Kwakel, The Netherlands. Plant were grown under average day temperatures of 18° to 24° C. and average night temperatures of 6° to 12° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from early May through October in The Netherlands.

*Plant habit.*—Broadly upright, overall globular in shape.

*Height and spread.*—Average 133.6 cm in height and 88.5 cm in diameter.

*Hardiness.*—At least in U.S.D.A. Zones 4 to 9.

*Disease and pest resistance.*—Not more susceptible or resistant to pests and diseases than other *Hydrangea macrophylla* cultivars.

*Root description.*—Fibrous, dense.

*Propagation.*—Softwood stem cuttings.

*Growth rate and vigor.*—Moderate to high.

Stem description:

*Stem shape.*—Round.

*Stem strength.*—Moderately strong.

*Stem aspect.*—Upright to an average angle of 50°.

*Stem color.*—Immature stem; 144C, mature stem; ranging between 199A and N199B.

*Stem size.*—Up to 125 cm in length and 8 mm in diameter.

*Stem surface.*—Smooth, moderately covered with narrow oblong lenticels, average of 2 mm in length and 1 mm in width, N186A in color.

*Branching.*—Moderately freely branching, including basal branching, with an average of 5 lateral branches, branching improves with pinching.

*Internode length.*—Average of 9.4 cm.

Foliage description:

*Leaf shape.*—Broad ovate.

*Leaf arrangement.*—Opposite.

*Leaf division.*—Simple.

*Leaf base.*—Short attenuate.

*Leaf apex.*—Short apiculate.

*Leaf margins.*—Serrate.

*Leaf venation.*—Pinnate, upper surface; 144B, lower surface; a blend of 144C and 145A.

*Leaf size.*—Average of 16.3 cm in length and 12.3 cm in width.

*Leaf attachment.*—Petiolate.

*Leaf surface.*—Upper surface; slightly glossy and slightly rugose, lower surface dull.

*Leaf color.*—Immature upper surface; slightly darker than 143A, immature lower surface; 143C to 144A, mature upper surface; N137A/B, mature lower surface; 138B.

*Petioles.*—Average of 4.6 cm in length and 4 mm in width, upper surface; 144A to 144B in color, lower surface; 144A in color, both surfaces are smooth and slightly glossy.

Inflorescence description:

*Inflorescence type.*—Mophead, compound corymb of rotate-shaped double sterile flowers composed of an average of 9 sepals, fertile flowers form buds that do not open.

*Lastingness of inflorescence.*—Persistent with color lasting about 3 weeks, fertile flowers self-cleaning.

*Inflorescence number.*—One per lateral or sublateral stem.

*Inflorescence size.*—Average of 9.5 cm in height and 16.1 cm in diameter.

*Flower number.*—An average of 200 sterile flowers and 45 fertile flowers per inflorescence.

*Flower fragrance.*—None.

*Flower aspect.*—Upright and outward.

*Flower size.*—Sterile flowers; rotate, average of 3.4 cm in diameter and 1.8 cm in depth, fertile flowers; campanulate, average of 1.5 mm in diameter and 3 mm in depth.

*Flower buds.*—Fertile flowers; an average of 3 mm in length and 1.5 mm in width, ovate in shape, 145A to 145B in color, sterile flowers; an average of 8 mm in length and 5 mm in diameter, ovate in shape and 75C to 75D tinged with 147D in color.

*Peduncles.*—Not present, pedicels attached to stem.

*Pedicels.*—Fertile flowers; An average of 1.5 mm in length and 0.7 mm in diameter, held at an average angle of 45° to vertical, 144B in color, moderate strength, moderately covered with very short hairs average length of 0.3 mm and N155D in color, sterile flowers; an average of 2.2 cm in length and 2 mm in diameter, held at an average angle of 40° to vertical, N77B in color, moderate strength, dull and moderately covered with very short hairs average length of 0.3 mm and N155D in color.

*Petals.*—Not present in sterile flowers or fertile buds (drop when opening).

*Sepals.*—Sterile flowers: Average of 9, rotate in arrangement, both surfaces smooth and dull, broad elliptic to obovate in shape, margin is entire, tip obtuse, base attenuate, an average of 1.8 cm in length and 1.1 cm in width, upper surface color when opening; 63D at base and 64D at tip, lower surface color when opening; 73D, upper surface when fully open; 75B, lower surface when fully open; 75B to 75 C, fading to upper side; 160A strongly tinged with 153D, fading to lower side; 148C strongly tinged with 160B, fertile flowers; 5, remain closed as fertile flower buds that do not open or develop, combined an average of 1.5 mm in diameter and 3 mm in depth, 145A to 145B in color, glabrous surface texture.

Reproductive organs:

*Androecium.*—Not present.

*Gynoecium.*—Sterile flowers; average of 4 pistils, 1.5 mm in length, stigma is club-shaped and N77D in color, style is about 1 mm in length and 75B to 75C in color, ovary is 70C, fertile flowers; stamens and pistils not present.

*Fruit and seed*.—No seeds or fruit observed to date.

It is claimed:

1. A new and distinct cultivar of *Hydrangea* plant named 'Inspire' substantially as herein illustrated and described.

* * * * *